US008131561B2

(12) United States Patent
Burke et al.

(10) Patent No.: US 8,131,561 B2
(45) Date of Patent: *Mar. 6, 2012

(54) INVENTORY TRACKING FOR ANATOMIC PATHOLOGY CONSULTATIONS

(75) Inventors: Mary Kay Burke, Portland, OR (US);
Joshua W. Arnold, Newton, MA (US);
Lori N. Cross, Kansas City, MO (US);
James L. Stroud, Savannah, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1130 days.

This patent is subject to a terminal disclaimer.

(21) Appl. No.: 11/422,779

(22) Filed: Jun. 7, 2006

(65) Prior Publication Data

US 2007/0288261 A1 Dec. 13, 2007

(51) Int. Cl.
*G06Q 50/00* (2006.01)
(52) U.S. Cl. .......................................................... 705/2
(58) Field of Classification Search .................. 705/2, 4;
340/572; 364/413.02; 700/99
See application file for complete search history.

(56) References Cited

U.S. PATENT DOCUMENTS

| 4,688,026 | A | * | 8/1987 | Scribner et al. ............... 235/385 |
| 5,216,596 | A | * | 6/1993 | Weinstein ...................... 348/79 |
| 6,006,191 | A | * | 12/1999 | DiRienzo ......................... 705/2 |
| 6,302,844 | B1 | | 10/2001 | Walker et al. |
| 6,606,413 | B1 | | 8/2003 | Zeineh |
| 2002/0068856 | A1 | | 6/2002 | Gelfand et al. |
| 2002/0135678 | A1 | | 9/2002 | Bacus et al. |
| 2002/0169637 | A1 | | 11/2002 | Akers et al. |
| 2004/0117046 | A1 | * | 6/2004 | Colle et al. ...................... 700/99 |
| 2004/0193449 | A1 | * | 9/2004 | Wildman et al. ................ 705/2 |
| 2005/0055240 | A1 | * | 3/2005 | Walsh et al. ..................... 705/2 |
| 2007/0136095 | A1 | * | 6/2007 | Weinstein ........................ 705/2 |

OTHER PUBLICATIONS

Non Final Office Action of U.S. Appl. No. 11/422,733 mailed Feb. 1, 2010.
Final Office Action mailed May 24, 2010 in U.S. Appl. No. 11/422,773.
Final Office Action mailed Feb. 16, 2011 in U.S. Appl. No. 11/442,773.
Advisory Action mailed Aug. 4, 2010 in U.S. Appl. No. 11/422,773.
Non-Final Office Action mailed Oct. 13, 2010 in U.S. Appl. No. 11/422,773.
Non-Final Office Action mailed Jul. 6, 2011 in U.S. Appl. No. 11/422,773.

* cited by examiner

*Primary Examiner* — Gerald J. O'Connor
*Assistant Examiner* — John Pauls
(74) *Attorney, Agent, or Firm* — Shook, Hardy & Bacon L.L.P.

(57) ABSTRACT

An on-line approach to coordinating intradepartmental anatomic pathology consultations, including coordinating access to physical case materials and/or electronic case materials, is provided. In accordance with one method in a clinical computing environment, a command to initiate a share event for an anatomic pathology case is received. One or more share recipients are determined manually and/or automatically for the share event. In addition, whether any physical case materials and/or electronic case materials are associated with the anatomic pathology case is determined. If any physical case materials and/or electronic case materials are associated with the anatomic pathology case, share recipient access to the materials is coordinated. After each share recipient reviews the case, the share recipient may enter comments.

13 Claims, 6 Drawing Sheets

INVENTORY TRACKING FOR ANATOMIC PATHOLOGY CONSULTATIONS

CROSS-REFERENCE TO RELATED APPLICATIONS

This application is related by subject matter to the invention disclosed in the commonly assigned application U.S. application Ser. No. 11/422,773, filed on even date herewith, entitled "COORDINATING ANATOMIC PATHOLOGY CONSULTATIONS AND INVENTORY TRACKING."

STATEMENT REGARDING FEDERALLY SPONSORED RESEARCH OR DEVELOPMENT

Not applicable.

BACKGROUND

The process of seeking input on challenging cases is an important element of the diagnostic process within an Anatomic Pathology (AP) department. Intradepartmental consultations play a key quality assurance role in the AP laboratory—they help to maximize the value of the complex and vital clinical information that AP provides to patient care, as well as being a crucial component of pathology training. In fact, performance of a high number of intradepartmental consultations has been used as a differentiator in pathology laboratories' marketing materials. A pathologist may seek consultation from colleagues while evaluating a difficult pathology result, when a patient's clinical history suggests closer scrutiny, or in other situations specified by departmental policies. The results of these intradepartmental consultations are an important part of the case documentation, contributing to the published results while remaining separate from them.

An increasingly valuable tool to the AP laboratory and intradepartmental consultations are physical case materials, such as slides and blocks of human tissue, for example, that are created for diagnostic evaluation of a case. Particularly for difficult or complex cases, these materials may be referred to again and again as the case evolves and as new testing methodologies become available.

An AP department must balance the competing priorities of seeking additional input on a case with the timely dissemination of results when managing and documenting intradepartmental consultations. Both information and physical case materials must be efficiently managed to maximize the value of the consultation process. The dynamic and collaborative nature of the consultation process, coupled with the time-sensitive nature of pathology results, make the consultation process a challenge for information systems to fully support.

A typical intradepartmental process flow can be described as follows. A pathologist determines that a consultation is desired, prepares a routing slip with the list of proposed consultants and collects the case materials relevant to the consultation, which are delivered to the first consultant on the routing. Each consultant in turn reviews the case materials and notes an opinion, and the consult materials are then delivered to the next consultant on the routing. Following the completion of the routing, the original pathologist documents a summary of the consultation in the case report and issues a final report.

This process is limited in a number of ways. For example, the sequential nature of the process requires manual "hand-offs" to keep the consultation moving between consultants. There is no mechanism for determining the status of a consultation or location of the physical case materials during the process and no ability to easily re-route a consultation to take advantage of other consultants' availability. In addition, there is no way to secure the information generated from the consultation during the process. Further, electronic access to consultation information is limited to that which may be entered on-line after the process is completed.

Another notable limitation of the typical process described above is that the determination of when to seek a consultation is left solely to the user. However, many departments may wish to identify situations where consultation should be routinely sought, based on standard criteria such as the type of case being diagnosed or the nature of the findings, such as a first-time malignant diagnosis. Also, departments may wish to institute additional levels of diagnostic review to take advantage of specialists (for example, all prostate biopsies are reviewed by the departmental genitourinary specialist), or as part of a quality initiative where all diagnoses of a certain type are reviewed. Under the typical process, it is also difficult to ensure compliance with existing departmental policies and to make use of the data generated by the process to further quality initiatives.

Accordingly, a system and method that provides a complete, end-to-end solution for initiating, managing, and documenting intradepartmental consultations is desirable. Additionally, a system and method for tracking physical case materials in conjunction with the consultations would be advantageous.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to an on-line approach to intradepartmental anatomic pathology consultations (referred to herein as share events) by providing computerized systems and methods for managing physical case inventory and consultation routing. Accordingly, in one aspect, the present invention is directed to a method, implemented at least in part in a clinical computing environment, for coordinating a share event for an anatomic pathology case. The method includes receiving a command to initiate the share event for the anatomic pathology case. The method also includes determining one or more share recipients for the share event. The method further includes identifying physical case materials associated with the anatomic pathology case. The method still further includes tracking the location of the physical case materials during the share event. The method also includes receiving at least one comment from at least one of the one or more share recipients.

Embodiments of the present invention further relate to a method, implemented at least in part in a clinical computing environment, for coordinating a share event for an anatomic pathology case. The method includes receiving a command to initiate the share event for the anatomic pathology case. The method also includes determining one or more share recipients for the share event. The method further includes determining whether any physical case materials and/or electronic case materials are associated with the anatomic pathology case. If any physical case materials and/or electronic case materials are associated with the anatomic pathology case, the method includes coordinating share recipient access to the physical case materials and/or electronic case materials during the share event. The method still further includes receiving at least one comment from at least one of the one or more share recipients.

In yet another aspect of the invention, embodiments are directed to a system for coordinating a share event for an anatomic pathology case. The system includes a share event initiation component, a case material tracking component, and a share comment component. The share event initiation component is capable of receiving a command to initiate a share event for one or more share recipients. The case material tracking component is capable of tracking access to any physical case materials and/or electronic case materials associated with the share event. The share comment component is capable of receiving at least one comment from at least one of the one or more share recipients.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention, among other things, address the unique demands of managing the intradepartmental consultation process within the anatomic pathology information system. Embodiments of the invention include a complete, end-to-end solution for initiating, managing, processing, and documenting intradepartmental consultations using a laboratory information system. Each instance of an interdepartmental consultation for an anatomic pathology case, in accordance with embodiments of the present invention, is referred to herein as a "share event." The pathologist responsible for a case or its report for which a share event is initiated is referred to herein as the "share initiator," while the pathologists or consultants who are requested to review a case are referred to herein as the "share recipients."

Exemplary Computing System Environment

Figure 1:
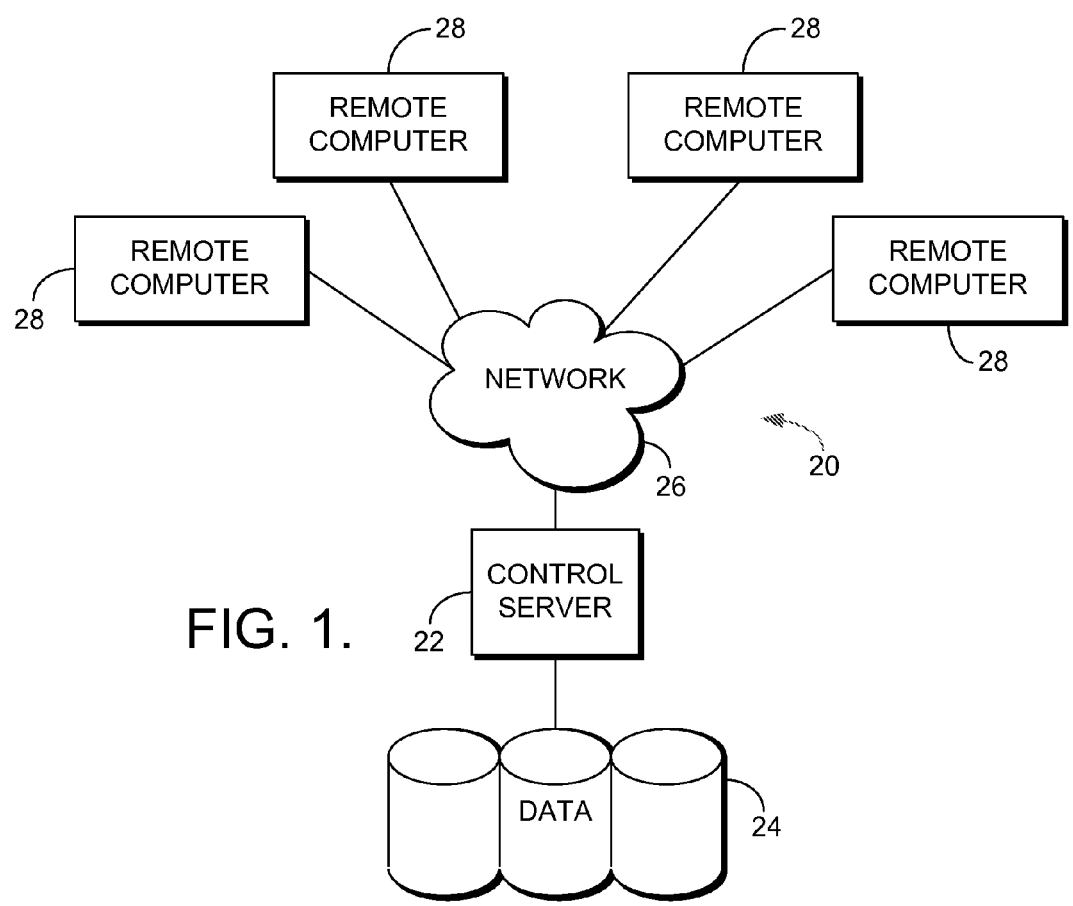
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Overall Consultation Process Flow

Figure 2:
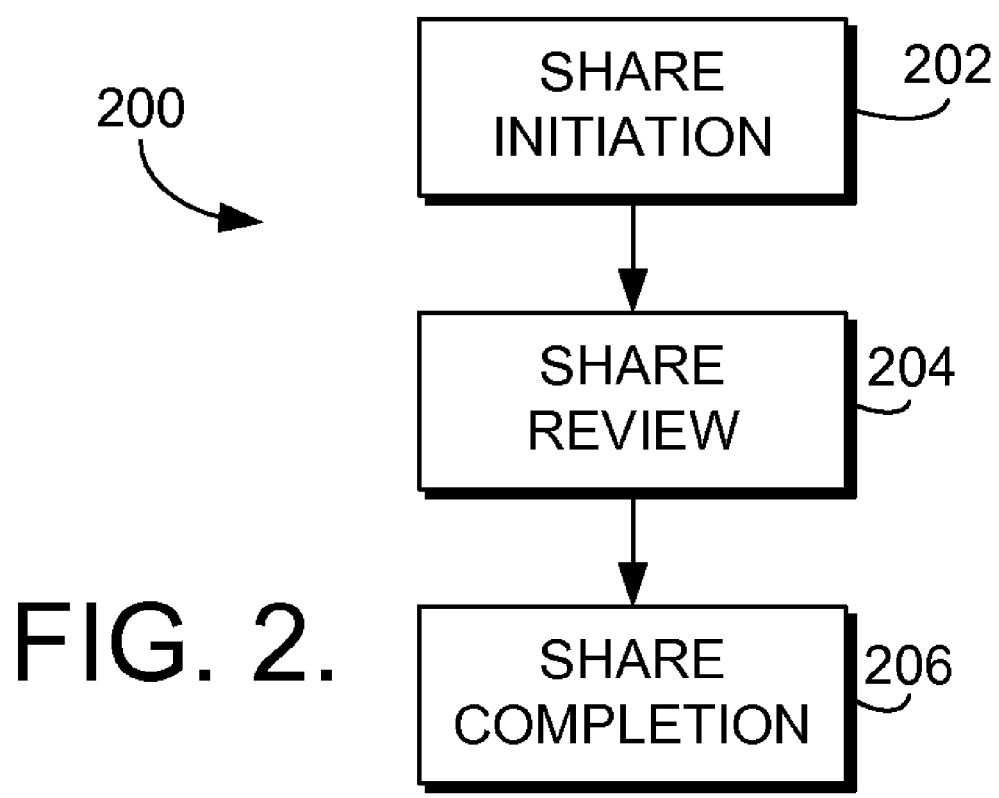
FIG. 2 is a flow diagram showing an overall method for coordinating a share event in accordance with an embodiment of the present invention.

Referring now to FIG. 2, a flow diagram is provided illustrating an overall process 200 for initiating and coordinating a share event in accordance with an embodiment of the present invention. Generally, the coordination of a share event can be broken into three broad steps. At the outset, a share event is initiated, as shown at block 202. As described in further detail below, a share event may be either manually or automatically initiated. If manually initiated, the pathologist who is responsible for a case or its report may wish to carry out an intradepartmental consultation and initiates the share event. Additionally, if rules are set forth defining conditions under which an intradepartmental consultation is required, the system may automatically initiate a share event. The initiation process may include a number of steps, including, for example, determining the members of the pathology staff or other consultants with whom the case will be shared (i.e. the share recipients), accessing data regarding the case, identifying physical case materials, determining a schedule for coordinating the consultation process, and including additional comments regarding the share event.

After a share event has been initiated, the review process may proceed, as indicated at block 204. Notification is sent to each of the pathologists or consultants identified as a share recipient, and an item appears in each share recipient's work queue with a special designation indicating that the share recipient has received a request to review the case for the share event. Each share recipient can either accept or decline the share request. The share recipients who accept the share request then may review the case data and physical case materials and record comments.

After each of the share recipients have provided comments, the share initiator is notified and the share event is marked complete, as represented by block 206. The share initiator may also choose to mark the share event complete before comments from all the share recipients have been entered. The share initiator may then review each of the comments and incorporate them into the final pathology report as appropriate. The full record of the share event is typically not incorporated in the final pathology report, but is instead stored in a pathology database for internal use only.

The share initiation, share review, and share completion steps are more fully discussed below.

Share Initiation

Figure 3:
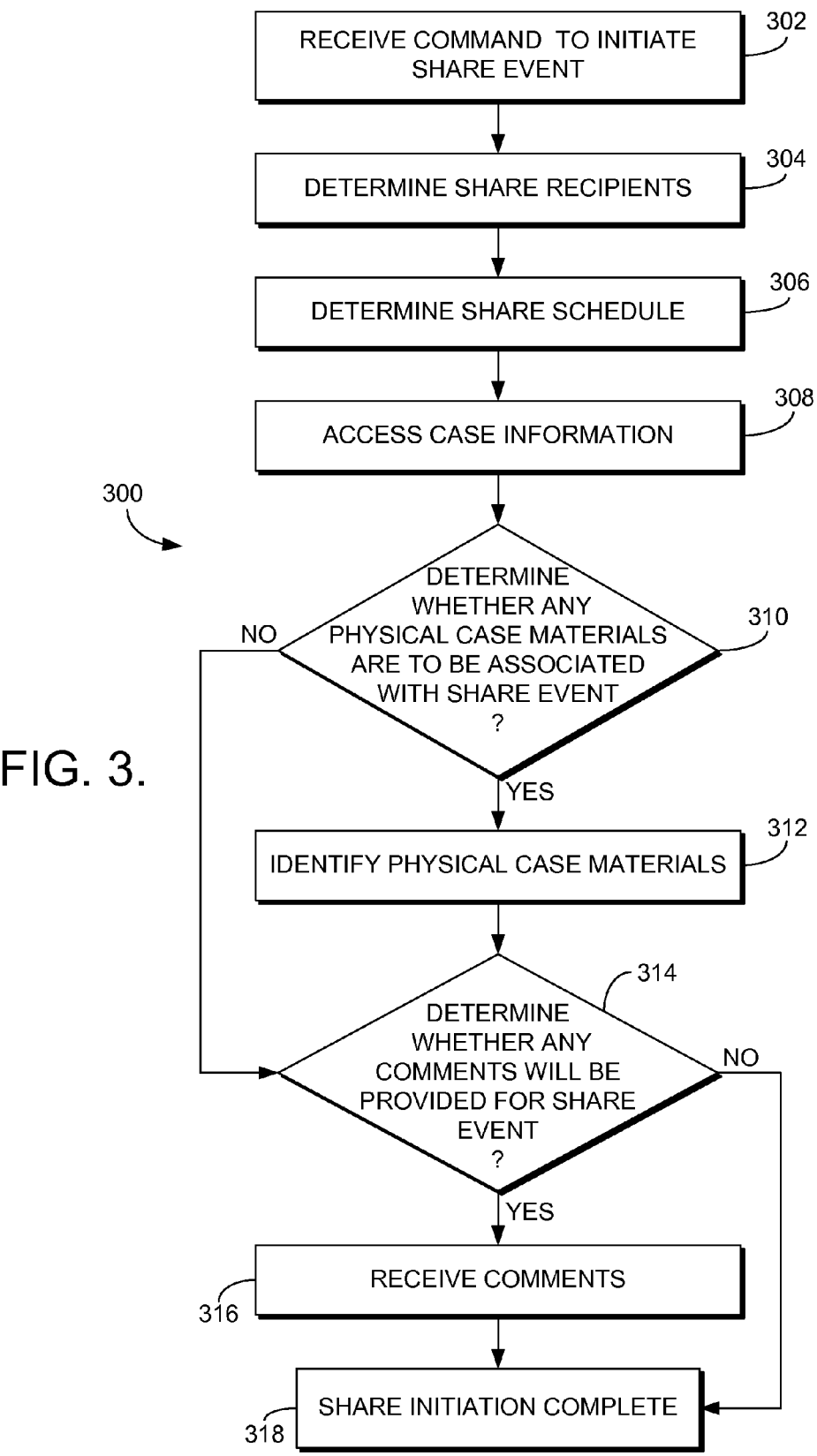
FIG. 3 is a flow diagram showing a method for initiating a share event in accordance with an embodiment of the present invention.

FIG. 3 provides a flow chart illustrating a more detailed method 300 for initiating a share event in accordance with an embodiment of the present invention. Initially, the system receives a command to initiate a share event, as shown at block 302. As mentioned previously, a share event may be either manually or automatically initiated. Manual initiation may occur when the pathologist who is responsible for a case or its report determines that an intradepartmental consultation is desired for the particular case. The pathologist, who is designated as the share initiator, may have ready access to the share initiation process through a case detail area on a report within the pathologist's work queue, which is the pathologist's primary tool for managing work in progress.

In addition to manual initiation, a share event may also be automatically initiated based on certain, pre-defined rules. For example, a pathology department may wish to identify and define situations in which a consultation should be routinely sought. The department then may set forth standard criteria, such as the type of case being diagnosed or the nature of the findings, that will trigger the initiation of a share event. In the case of an automatic initiation, the system may prompt the pathologist responsible for the case, who is designated as the share initiator, to provide any necessary information prior to initiating the share event.

After receiving an indication that a share event is being initiated, the share recipients for the share event are determined, as shown at block 304. As mentioned previously, these are the pathologists or consultants with whom the case will be shared and who may choose to review the case and provide comments. Designating share recipients may be a manual or automatic process. For example, the share initiator may manually choose the pathologists or other consultants that the share initiator wishes to review the case and identify such desired consultants to the system (e.g., through data entry or the like). Alternatively or additionally, the system may automatically designate pathologists or consultants as share recipients for the case. The automatic designation may be based on a variety of factors, including, for instance, the type/nature of the case being evaluated and the availability of the various pathologists or consultants. For example, a department may designate "subject experts" to whom specific types of consults are directed automatically, such as a dermatopathologist who is responsible for reviewing all new melanoma diagnoses.

The pathologists or consultants included as available share recipients for a share event may be controlled by the system in various embodiments of the invention. Typically, only pathologists within a particular health system will be included as potential share recipients. However, an external consultant list could be provided to accommodate consultations sent outside the health system. In some embodiments, the system may include multi-facility filtering that allows only those pathologists within certain areas of the health system to be designated as share recipients for a case. Further, typically only active personnel are included as available share recipients. Any and all such variations are contemplated to be within the scope of embodiments of the present invention.

After the share recipients are determined, a schedule may be determined for the share event, as shown at block 306. The detail of the share schedule may vary greatly within the scope of the invention. Typically, at a minimum, a due date/time for completion of the share event will be determined. The due date/time may be manually set by the share initiator or may be controlled by a pre-determined period, such as a site specific standard turnaround time, for example.

In some embodiments, the system may determine an order in which the share recipients will review the case and may further define a time period for each share recipient's review. In doing so, the system may be able to take into account a variety of information to determine the share schedule. For example, the system may have access to calendar and availability information for the share recipients and set a schedule based on the information. In addition, the system may account for the physical proximity between share recipients in determining an order to reduce time lag between reviews. Further, the capabilities and expertise of the share recipients may be considered in determining a share schedule. For example, it may be desirable to schedule share recipients with particular expertise first depending on the type of case being reviewed to ensure that their comments are provided in a timely manner.

As shown at block 308, the system may also access case information that may assist each share recipient in the performance of his/her review. For example, the system may access electronic records, such as patient records and the like, that may be provided to each share recipient.

In addition to the case information, physical case materials may also be associated with the share event. Accordingly, at block 310, whether any physical case materials are to be associated with the share event is determined. The physical case materials may be any type of material that is created for diagnostic evaluation of a case. For example, the physical case materials may include a microscopic slide of tissue from a patient or an electrophoresis gel. If physical case materials are to be tracked as part of the consultation process, those materials are identified, as shown at block 312. In some embodiments, the system may prompt the share initiator to determine and identify any physical case materials (e.g., though entry of an identifier of the physical case materials or the like). In other embodiments, the system may be capable of automatically determining and identifying physical case materials (or the electronically stored representations of the materials) to be associated with the share event (e.g., by searching a database of physical case materials).

At block 314, whether any comments will be provided as part of the consultation process is determined. The comments may include, for instance, additional information regarding the share event, such as the reason for initiating the event or the nature of the case. If it is determined that comments are to be provided for the share event, the system accesses/receives the comments, as shown at block 316. In some embodiments, the system may automatically determine that comments are to be provided and may access those comments based on pre-defined rules. For example, in the case that the share event is automatically initiated by some triggering condition, the system may automatically provide the reason for initiating the share event. Additionally or alternatively, the system may prompt the share initiator to provide any comments, and the share initiator may manually enter comments (e.g., through data entry or the like). The share initiation process is completed at block 318.

Once a share event has been initiated, the open reports on the anatomic pathology case are automatically placed on a "Hold" status. In addition, an indication, such as "Hold for share results," may be provided for the case. Accordingly, an individual reviewing the case will be able to recognize that a share event is being conducted for the case and that a final report in the case will be issued after the share event has been completed.

Share Review

The review portion of a share event may be performed in a number of different ways within the scope of the present invention. The following discussion provides only a few exemplary methods for coordinating share recipient reviews during a share event, including the tracking of physical case materials, and should not be viewed as limiting. The first exemplary method discussed below illustrates a process in which share recipients are sequentially designated as the owner of the share event and physical case materials are tracked to the current share owner for review. The second exemplary method below illustrates a process in which the physical case materials are checked into a repository from which each share recipient may request the physical case materials for performing his/her review. The third exemplary method discussed below illustrates a process in which the case materials may be represented in an electronic format, allowing concurrent review by each of the share recipients.

Figure 4:
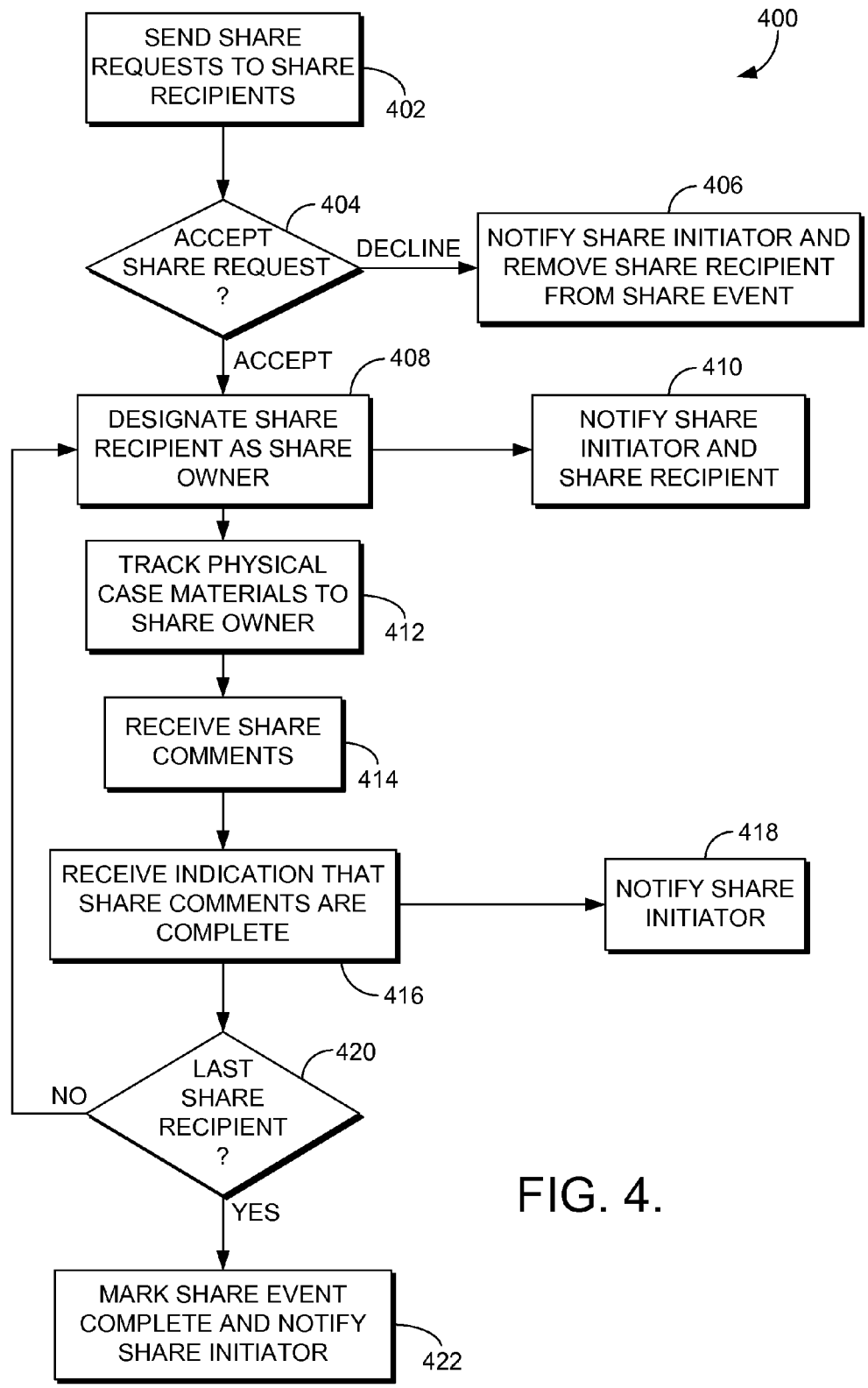
FIG. 4 is a flow diagram showing a method for coordinating the sequential review of an anatomic pathology case by share recipients in accordance with an embodiment of the present invention.

Turning to FIG. 4, a flow diagram is provided illustrating an exemplary method 400 for coordinating share reviews and tracking physical case materials in accordance with an embodiment of the present invention. Initially, as shown at block 402, the system sends a share request to each of the designated share recipients. Each share recipient can either accept or decline the share request, as shown at block 404, and the response is made available to the share initiator. Each share request remains in a pending status until the corresponding share recipient responds. If a share recipient declines a share request, the system notifies the share initiator and removes the share recipient from the share event, as shown at block 406. Even if a share recipient accepts a share request, the share recipient may later be removed from the share event either by the share initiator or the share recipient.

In some embodiments, if a share recipient declines a share request, a designee for that share recipient may be indicated either manually or automatically. For example, some cases may require review by a pathologist having a particular specialty. In such a case, if the pathologist with that specialty who was indicated as a share recipient declines the share request, another pathologist may be designated. Further, in some embodiments, a share request may be sent to a pool of share recipients (e.g., a number of pathologists having a particular specialty), any one of which may accept the share request.

One share recipient will be designated as the current share owner at all times during the share event. Accordingly, at block 408, a share recipient who has accepted the share request is designated as the first share owner. The designation of the first share owner may be performed in a number of different ways. For example, if a schedule is determined during the share initiation process that sets an order for the share recipients to review the case, the first share recipient from that order is designated as the share owner. As another example, the first recipient to accept the share request may be designated as the share owner. Further, the system may randomly assign a share recipient as the first share owner. In some embodiments, a notification may be sent to both the share initiator and the share recipient, indicating the share recipient's designation as the share owner, as shown at block 410.

The physical case materials are tracked to the current share owner, as shown at block 412. Typically, the share initiator is responsible for having the materials physically delivered to the share owner, but in some cases, the share owner may be responsible for obtaining the materials. Tracking of the physical case materials by the system may be performed a number of different ways within the scope of the invention. For example, in one embodiment, the physical case materials may be automatically tracked to the current share owner, regardless of whether the share owner currently has possession of the physical case materials. In another embodiment, the system may require a manual indication to be provided before tracking the physical case materials to a particular location (e.g., the current share owner). For example, the share initiator or share owner may access the system and indicate the current location of the physical case materials. In yet another embodiment, automatic location-based tracking means, such as a radio-frequency (RF) system and an RFID placed on the materials, for instance, may be used to track the actual location of the physical case materials at all times.

The share owner may then review the data associated with the case, including the physical case materials, and input comments regarding the case into the system, as shown at block 414. Each of the share recipients has access to all case and report data for the case being shared. In some embodiments, the share event may be configured to be a "blind" event, in which each share recipient does not have access to others' interpretations and comments. In other embodiments, the share event may be configured as an "open" event, in which a more collaborative approach is taken and share recipients may view comments entered by other share recipients.

Once the share owner has completed his/her review, the share owner may mark the comments as complete, as shown at block 416. In some embodiments, the system may notify the share initiator that the share recipient has entered comments and marked the comments complete, as shown at block 418.

The system next may determine whether the current share owner is the last share recipient, as shown at block 420. If the current share owner is the last share recipient, the share event is marked complete, and the share initiator is correspondingly notified, as shown at block 422. Alternatively, if the current share owner is not the last share recipient, a new share recipient is designated as the current share owner. In some embodiments, the previous share owner may select and designate the share recipient to be the next share owner. In other embodiments, the system automatically selects the next share owner. For example, the system may select the next share owner based on an order that was predetermined during the share initiation process. Additionally, the system may select the next share owner on an on-going basis dependent upon a variety of different information, such as current availability information for each of the share recipients, for example. The process described with reference to block 408 through block 418 is then repeated for the current share owner. Typically, the previous share owner is responsible for having the physical case materials transferred to the next share owner, but in various embodiments, the share initiator or the next share owner may be responsible for the transfer. As discussed previously, tracking of the physical case materials may be manual (e.g., input by the previous share owner, new share owner, and/or share initiator) or automatic (e.g., automatic tracking by share owner designation or via an automatic tracking system, such as use of RFID).

In some embodiments, a share recipient may opt to request ownership of the share event before it has been passed to that share recipient. If such a request is accepted (e.g., by the current share owner and/or share initiator), the requesting share recipient is designated as the share owner and the physical case materials are sent and tracked (manually or automatically) to that share recipient. Information regarding the tracking of the physical case materials and share ownership during the share event is available to the share initiator, as well as each of the share recipients, to facilitate rapid reassignment of the share ownership as the share recipients' schedules change throughout the process.

Figure 5:
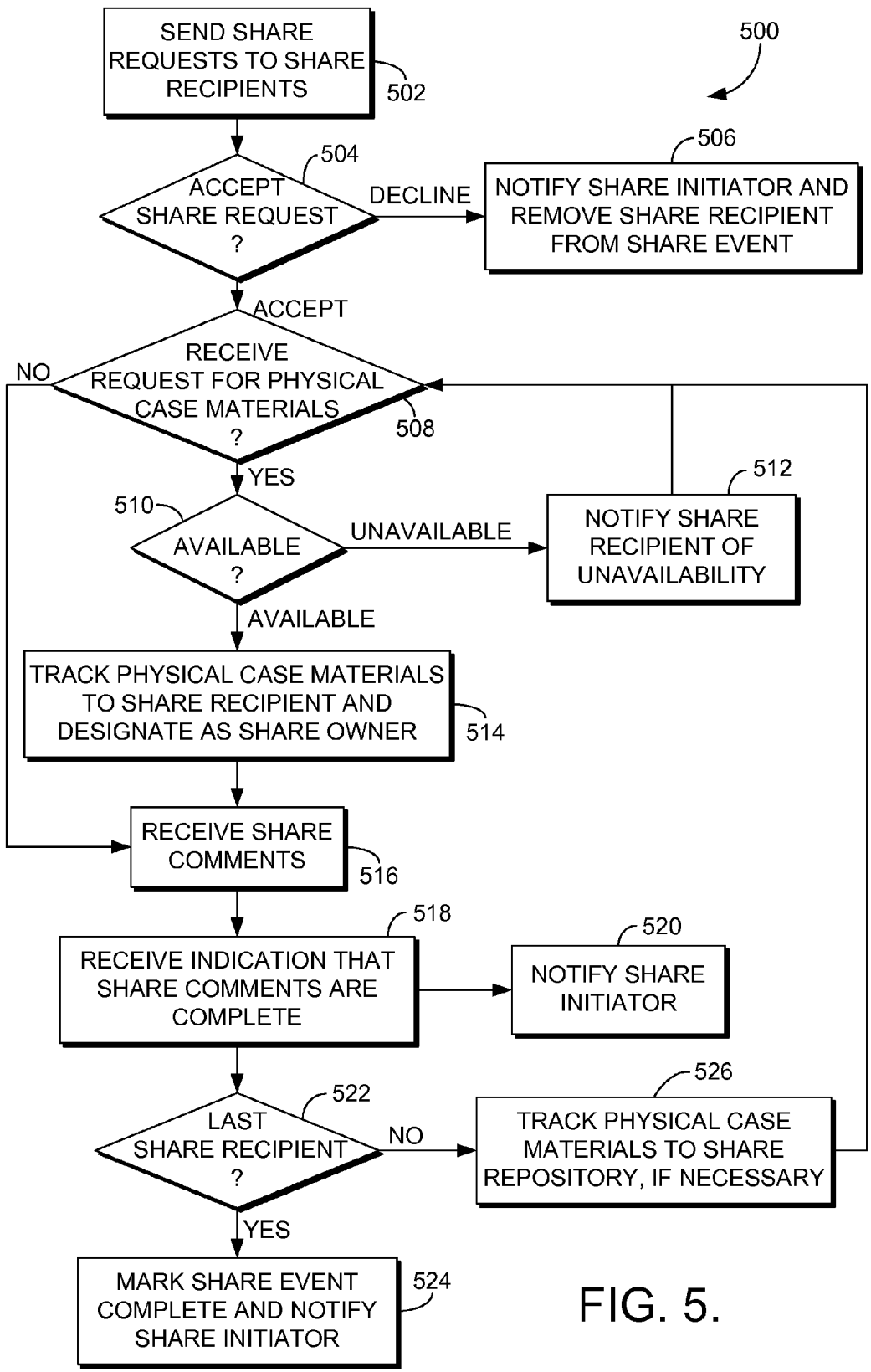
FIG. 5 is a flow diagram showing a method for coordinating a share event by providing a repository for physical case materials in accordance with an embodiment of the present invention.

Referring now to FIG. 5, a flow diagram is provided showing a method 500 for coordinating a share event by providing a repository for physical case materials. In such an embodiment, the physical case materials associated with an anatomic pathology case may be requested from the repository and reviewed by each share recipient. Initially, as shown at block

502, each share recipient receives a share request. The share recipient may either accept or decline the share request, as shown at block 504. If the share recipient declines the share request, a notification may be sent to the share initiator and the share recipient is removed from the share event, as shown at block 506.

If a share recipient accepts the share request, the share recipient may request the physical case materials from the share repository at any time during the share event. Accordingly, as shown at block 508, the system may receive a request for the physical case materials from a share recipient. In some cases, a share recipient may not wish to review the physical case materials and may proceed with providing share comments, as shown at block 516. Alternatively, if a share recipient requests the physical case materials, the system determines whether the physical case materials are available, as shown at block 510. If the physical case materials are currently tracked to another share recipient or are otherwise unavailable, the system notifies the requesting share recipient of their unavailability, as shown at block 512. The share recipient may then either wait until they are made available or may proceed to entering comments without reviewing the physical case materials, as desired.

Alternatively, if the physical case materials are available in the repository, the materials are tracked to the requesting share recipient, who is also designated as the share owner, as shown at block 514. The share owner may then review the case data, including the physical case materials, and enter comments into the system, as shown at block 516. Once the share owner has completed the review, the comments are marked as complete, as shown at block 518. The system may notify the share initiator that the share recipient's comments are complete, as shown at block 520.

After a share recipient marks the comments as complete, the system determines whether the share recipient is the last share recipient scheduled to provide comments, as shown at block 522. If the last share recipient has provided comments, the system marks the share event as complete and notifies the share initiator, as shown at block 524. Additionally, if the physical case materials are currently checked out of the repository, the materials may be tracked back to either the share repository or to the share initiator. The share recipient who has the materials, the share initiator, or another individual may be responsible for physically delivering the case materials.

Alternatively, if the share recipient marking his/her comments as complete is not the last share recipient to provide comments, the process of receiving share comments is repeated. If the share recipient had reviewed the physical case materials and been designated as the share owner, the system tracks the physical case materials back to the share repository and removes the share owner designation from the share recipient, as shown at block 526. In addition, the system may notify the other share recipients, as well as the share initiator, that the physical case materials have been returned to the repository. When another share recipient requests the physical case materials, the process described with reference to block 508 through 522 is then repeated.

As mentioned previously, a share recipient may request the physical case materials and to be designated as the share owner at any time during the share event even if another share recipient currently has the physical case materials and is designated as the share owner. If the request is accepted (e.g., by the current share owner and/or the share initiator), the requesting share recipient is designated as the share owner and the physical case materials are tracked to the share recipient. Tracking of the physical case materials to the requesting share recipient may be either manual or automatic as previously described.

Figure 6:
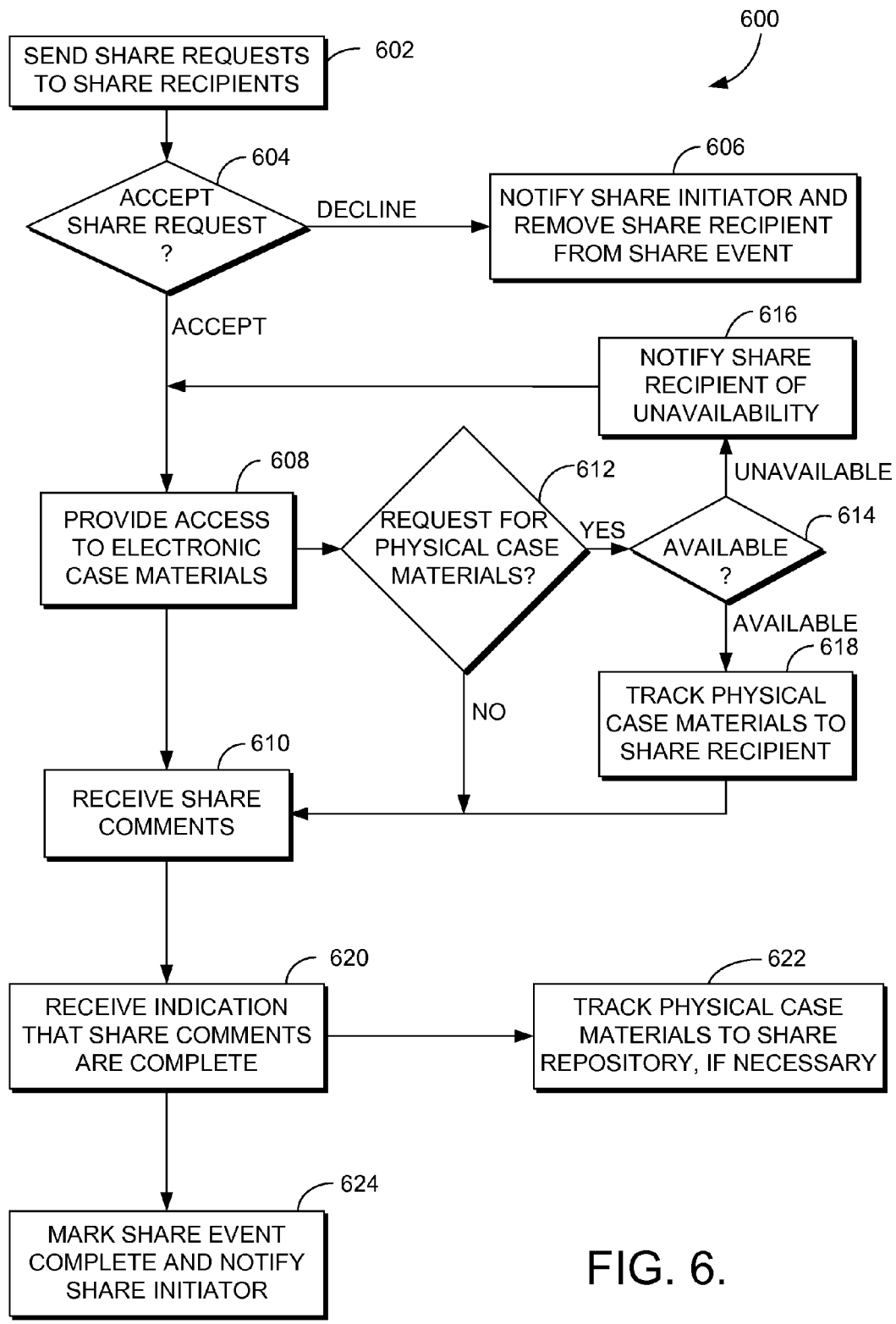
FIG. 6 is a flow diagram showing a method for coordinating a share event in which an electronic form of the physical case materials is available for share recipients to review in accordance with an embodiment of the present invention.

In some embodiments of the present invention, an electronic form of the physical case materials may be available. For example, pathology slides may be scanned, and the scanned images may be reviewed by consultants. The electronic access to the physical case materials may provide a truly non-linear consultation process in which each share recipient can concurrently access the case information (including the electronic form of the physical case materials) and provide comments at any point the share event is active. Accordingly, FIG. 6 provides a flow diagram illustrating a method 600 for coordinating a share event in which an electronic form of the physical case materials is available in accordance with an embodiment of the present invention. Initially, as shown at block 602, the system sends a share request to each of the determined share recipients. Each share recipient may choose to accept or decline the share request, as shown at block 604. If a share recipient declines a share request, a notification may be sent to the share initiator and the share recipient is removed from the share event, as shown at block 606.

If a share recipient accepts the share request, the share recipient may review the data associated with the case, including the electronic form of the physical case materials. Accordingly, the share recipient is provided access to the electronic case materials, as shown at block 608. Because an electronic form of the physical case materials is available, each of the share recipients may concurrently review the information. A share recipient may or may not wish to also review the physical case materials, as shown at block 612. If the share recipient does not need to review the physical case materials, the share recipient may enter comments, as shown at block 610, and mark the comments as complete, as shown at block 620.

In some cases, however, a share recipient may wish to examine the actual physical case materials in addition to the electronic representation and request the physical case materials, as shown at block 612. Accordingly, as shown at block 614, after the system receives a request for the physical case materials, the system determines whether the physical case materials are currently available. The physical case materials may typically be stored in a repository. If the physical case materials are not available, the system notifies the requesting share recipient, as shown at block 616. The share recipient may then either wait until they are made available or proceed to entering comments without the physical case materials. In some embodiments, the system may provide a notification to the share recipient when the materials become available. In addition, as mentioned previously, a share recipient may request and obtain the physical case materials from another share recipient.

Alternatively, if the physical case materials are available, they are tracked to the requesting share recipient, as shown at block 618 (e.g., by manually or automatically tracking the materials as previously described). The share recipient may review the physical case materials and provide comments, as shown at block 610, and mark the comments complete, as shown at block 620. The physical case materials may then be tracked back to the share repository, as shown at block 622. After all of the share recipients have reviewed the case information and provided comments, the share event is marked as completed and the share initiator is notified, as shown at block 624.

Share Completion

As indicated previously, a share event will automatically be marked complete when all accepted share requests on the share event have been marked complete by the corresponding share recipients. Alternatively, when a share event has received share comments from at least one share recipient, the share initiator can manually mark the share event complete. Marking the event complete will remove any incomplete share requests from the corresponding share recipients' work queues.

Share events become overdue when their due date/time is reached. At a pre-defined point (e.g., a certain number of hours prior to due date/time), a message may be sent to any remaining share recipients who have not completed their comments. A share timer may also be used to monitor the amount of time each share recipient maintains ownership of the share event, and will send an alarm to the share recipient and the share initiator when a pre-determined consultation time limit is nearly reached.

Once a share event is complete, the shared case's reports are automatically removed from a "Hold" status. The physical case materials may be tracked back to the share initiator or the repository (i.e. via manual or automatic tracking as described previously). The share initiator may then review the consulting comments and render a final report on the case, documenting the fact that the share event occurred and including comments from the various share recipients at his/her discretion.

Share Viewing, Maintenance and Security

The share initiator may be able to view all information entered for a share event at any time during the process, including all share recipients' comments, date/time of entry, and history of share ownership. The share initiator may access and maintain the share event from a specific folder on his/her work queue. In addition, the share initiator can add additional share recipients, remove recipients who have not entered comments, or cancel the share event at any time.

When a share event is canceled, the share is removed from all share recipients' work queues and is no longer editable by any users. Canceled share events may typically be viewable by the share initiator only (e.g., via a "Show Canceled" option available on the work queue).

The share recipients may also be able to view a variety of different information regarding the shared case. As mentioned previously, the share event may be either a "blind" event, in which share recipients cannot view others' comments, or an "open" event, in which share recipients may view others' comments. In addition, in some embodiments, the share recipients may access share history information, including physical case material tracking information. Further, in some embodiments, the recipients may have the ability to view the completed share event in its entirety once it is marked complete.

Data Requirements Overview

One or more databases may be used to store data regarding share events. Share events may be stored at the case level, and one or more instances of share events per case may be supported. A variety of information may be recorded for each share event, including, for example, date/time initiated, user who initiated (share initiator), list of share requests associated with the share event (i.e. names of share recipients), identification of current share owner (one share recipient at any given time), share due date, share completion date, reason for share, and share initiator comments. A share status field may also be maintained (e.g., indicating either in process, completed, or canceled).

Each share recipient has access to his/her own share request, which may include a consultation comments field with a date/time stamp and a status (e.g., pending, pending/owner, declined, complete). While in some embodiments share recipients may be able to view other share recipients' comments, the share recipients may not have access to modify other share recipients' comments.

A pending/owner status may identify the current share owner as well as the current location of the physical case materials. The history of the share ownership (date/time stamp of all ownership changes) is typically available for viewing by the share initiator and all share recipients involved in the share event and may be used to review the case materials tracking as well.

Share events may be identified on the share initiator's work queue, while share requests are identified on each share recipient's work queue. Reports associated with cases currently being shared may also be identified as being associated with open share events when viewed on work queues.

Conclusion

As can be understood, the present invention provides systems and methods for coordinating share events for anatomic pathology consultations, including tracking physical case materials for each share event.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions that, when used by one or more computing devices, cause the one or more computing devices to perform a method for coordinating a share event for an anatomic pathology case, the method comprising:

receiving a command to initiate the share event for the anatomic pathology case;

determining a pool of share recipients to include in the share event;

sending a notification to each of the pool of share recipients, wherein the notification includes a special designation in each share recipient's work queue indicating that a request to review the share event for the anatomic pathology case has been received;

determining a plurality of share recipients, based on the share recipients who accept the share request, for the share event;

considering capabilities and expertise of the plurality of share recipients;

identifying physical case materials associated with the share event for the anatomic pathology case;

based on the consideration, determining a schedule for the plurality of share recipients to review the anatomic pathology case, the schedule including an order of review by the plurality of share recipients facilitating sequential review of the physical case materials;

defining a time period for each share recipient's review;

monitoring the amount of time each share recipient maintains ownership of the share event for the anatomic pathology case;

notifying the share recipient or share initiator when the time period is nearly reached;

tracking the location of the physical case materials for the anatomic pathology case during the share event;

receiving at least one comment from at least one of the plurality of share recipients after reviewing the anatomic pathology case.

2. The one or more computer storage media of claim 1, wherein receiving a command to initiate the share event comprises:

providing one or more rules defining when a share event is to be initiated; and determining that the share event is to be initiated based on at least one of the one or more rules.

3. The one or more computer storage media of claim 1, wherein at least one of the plurality of share recipients is determined based on user input.

4. The one or more computer storage media of claim 1, wherein at least one of the plurality of share recipients is automatically determined based on one or more pre-defined criteria.

5. The one or more computer storage media of claim 1, wherein identifying physical case materials associated with the anatomic pathology case comprises receiving a user-specified identification of the physical case materials.

6. The one or more computer storage media of claim 1, wherein tracking the location of the physical case materials during the share event comprises receiving a manual indication of the location of the physical case materials.

7. The one or more computer storage media of claim 1, wherein tracking the location of the physical case materials during the share event comprises:

identifying one of the plurality of share recipients as a share owner; and identifying the location of the share owner as the location of the physical case materials.

8. The one or more computer storage media of claim 1, wherein tracking the location of the physical case materials comprises:

placing an RFID on the physical case materials; and tracking the location of the physical case materials using the RFID.

9. The one or more computer storage media of claim 1, wherein tracking the location of the physical case materials comprises:

providing a repository for the physical case materials; and tracking the physical case materials to one of the plurality of share recipients when the one of the plurality of share recipients removes the physical case materials from the repository.

10. One or more computer storage media storing computer-useable instructions that, when used by one or more computing devices, cause the one or more computing devices to perform a method for coordinating a share event for an anatomic pathology case, the method comprising:

receiving a command to initiate the share event for the anatomic pathology case;

determining a pool of share recipients to include in the share event;

sending a notification to each of the pool of share recipients, wherein the notification includes a special designation in each share recipient's work queue indicating that a request to review the share event for the anatomic pathology case has been received;

determining a plurality of share recipients for the share event, based on the share recipients who accept the share request;

identifying physical case materials associated with the anatomic pathology case;

identifying electronic case materials corresponding with the physical case materials associated with the anatomic pathology case;

considering capabilities and expertise of the plurality of share recipients;

based on the consideration, coordinating share recipient access to the physical case materials for the anatomic pathology case during the share event; and receiving at least one comment from at least one of the plurality of share recipients after reviewing the anatomic pathology case.

11. The one or more computer storage media of claim 10, wherein providing the plurality of share recipients access to the electronic case materials comprises allowing the plurality of share recipients to simultaneously access the electronic case materials.

12. The one or more computer storage media of claim 11, wherein coordinating share recipient access to the physical case materials comprises:

receiving a request for the physical case materials from a share recipient;

determining if the physical case materials are available; and if the physical case materials are available, allowing the share recipient to access the physical case materials.

13. A system, including one or more processors and one or more computer storage media, for coordinating a share event for an anatomic pathology case, the system comprising:

a share event initiation component for receiving a command to initiate a share event for the anatomic pathology case for a plurality of share recipients, determining a pool of share recipients to include in the share event, sending a notification to each of the pool of share recipients, wherein the notification includes a special designation in each share recipient's work queue indicating that a request to review the share event for the anatomic pathology case has been received, and determining a plurality of share recipients, based on the share recipients who accept the share request, for the share event;

a case material tracking component for tracking access by the plurality of share recipients to physical case materials for the anatomic pathology case associated with the share event, wherein the case material tracking component designates one of the plurality of share recipients as a share owner, based on a consideration of capabilities and expertise of the plurality of share recipients, and identifies the physical case materials for the anatomic pathology case as being located with the share owner, and further wherein the case material tracking component defines a time period for each share recipient's review a share timer for monitoring the amount of time each share recipient maintains ownership of the share event for the anatomic pathology case and sending an alarm to the share recipient or share initiator when the time period is nearly reached; and a share comment component for receiving at least one comment from at least one of the plurality of share recipients after reviewing the anatomic pathology case.

* * * * *